United States Patent
Andersen

(10) Patent No.: US 10,442,765 B2
(45) Date of Patent: *Oct. 15, 2019

(54) METHOD FOR PRODUCING 2,3-DICHLORO-5-(TRICHLOROMETHYL) PYRIDINE

(71) Applicant: Cheminova A/S, Harboøre (DK)

(72) Inventor: Casper Stoubeak Andersen, Lemvig (DK)

(73) Assignee: Cheminova A/S, Harboøre (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/802,662

(22) Filed: Nov. 3, 2017

(65) Prior Publication Data

US 2018/0057459 A1    Mar. 1, 2018

Related U.S. Application Data

(63) Continuation of application No. 14/898,416, filed as application No. PCT/DK2014/050166 on Jun. 13, 2014, now Pat. No. 9,809,543.

(30) Foreign Application Priority Data

Jun. 14, 2013  (DK) .................................. 2013 70319
Mar. 20, 2014  (DK) .................................. 2014 70138

(51) Int. Cl.
  *C07D 213/61*   (2006.01)
  *C07D 213/643*  (2006.01)
  *C07D 213/74*   (2006.01)

(52) U.S. Cl.
  CPC ....... *C07D 213/61* (2013.01); *C07D 213/643* (2013.01); *C07D 213/74* (2013.01)

(58) Field of Classification Search
  CPC .................................................. C07D 213/61
  See application file for complete search history.

(56) References Cited

U.S. PATENT DOCUMENTS

| 4,241,213 A | 12/1980 | Nishiyama et al. |
| 4,309,548 A | 1/1982 | Wilson |
| 4,324,627 A | 4/1982 | Cartwright |
| 4,331,811 A * | 5/1982 | Werner .................... B01J 31/20 |
| | | 546/345 |
| 4,419,514 A | 12/1983 | McKendry et al. |
| 4,634,771 A | 1/1987 | Shim et al. |
| 4,636,565 A | 1/1987 | Werner et al. |
| 4,672,125 A | 6/1987 | Gray et al. |
| 4,833,250 A | 5/1989 | Bay |
| 4,897,488 A | 1/1990 | Gallenkamp et al. |
| 4,958,025 A | 9/1990 | Jelich |
| 5,229,519 A | 7/1993 | Zhang et al. |
| 5,484,929 A | 1/1996 | Toomey |
| 6,921,828 B2 | 7/2005 | Dann et al. |

FOREIGN PATENT DOCUMENTS

| CN | 101092392 A | 12/2007 |
| EP | 4414 A1 | 10/1979 |
| EP | 0 110 690 A1 | 6/1984 |
| EP | 0246349 A1 | 11/1987 |
| EP | 281965 A1 | 9/1988 |
| GB | 2002368 A | 2/1979 |
| WO | 9413640 A1 | 6/1994 |
| WO | 2007/060662 A2 | 5/2007 |

* cited by examiner

*Primary Examiner* — Andrew D Kosar
*Assistant Examiner* — John S Kenyon
(74) *Attorney, Agent, or Firm* — Harness, Dickey & Pierce, P.L.C.

(57) ABSTRACT

The present invention relates to a novel process for producing of 2,3-dichloro-5-(trichloromethyl)pyridine by using $PCl_5$ as chlorinating agent at elevated temperature and pressure.

34 Claims, No Drawings

METHOD FOR PRODUCING 2,3-DICHLORO-5-(TRICHLOROMETHYL) PYRIDINE

CROSS-REFERENCE TO RELATED APPLICATIONS

This application is a continuation of U.S. patent application Ser. No. 14/898,416 filed on Dec. 14, 2015, now U.S. Pat. No. 9,809,543, issued: Nov. 7, 2017, which is a National Stage of International Application No. PCT/DK2014/050166, filed Jun. 14, 2014. The entire disclosure of each of the above applications is incorporated herein by reference.

INTRODUCTION

The present invention relates to a novel process for producing the compound 2,3-dichloro-5-(trichloro methyl) pyridine.

BACKGROUND 2,3-dichloro-5-(trifluoromethyl)pyridine (DCTF) is an important organic intermediate for the agrochemical industry in particular for use in the synthesis of fluazinam and fluopicolide as well as other pesticidal active pyridine compounds, e.g. as disclosed in the following patent specification nos. WO 2007/060662-A2, U.S. Pat. No. 6,921,828, and GB 2002368-A. The precursor for this molecule is 2,3-dichloro-5-(trichloromethyl)pyridine (PCMP).

Several methods for production of DCTF are described in the literature, including the use of different starting materials such as 6-hydroxynicotinic acid, 3-picoline, or 2-chloro-5-chloromethylpyridine, routes that pass a common intermediate, i.e. PCMP, towards the final DCTF product.

The production of DCTF starting from 3-picoline-N-oxide can be accomplished by a 4 step synthesis route. The first step of the synthesis is disclosed in U.S. Pat. No. 4,897,488 wherein 2-chloro-5-methylpyridine is synthesized, followed by a radical chlorination step e.g. as described in U.S. Pat. No. 4,241,213, followed by formation of PCMP e.g. as disclosed in U.S. Pat. No. 4,331,811, whereas the final step to DCTF is disclosed in European patent publication number EP 110690-A1.

There are several known methods for the preparation of PCMP, e.g. starting from 2-chloro-5-(trichloromethyl)pyridine using chlorine gas optionally in the presence of various metal based catalysts e.g. as described in U.S. Pat. Nos. 4,636,565, 4,331,811, 4,309,548 and European patent application no. EP 246349-A1. 2-chloro-5-(trichloromethyl)pyridine can be prepared according to the procedure disclosed in U.S. Pat. No. 4,324,627 and European patent application no. EP 4414-A1.

Chlorination of cyanopyridines directly on the pyridine ring is disclosed in patent publication nos. WO 9413640-Al and U.S. Pat. No. 5,484,929.

Methods for the preparation of 3-trichloromethylpyridines starting from nicotinic acid using various chlorinating agents are described in the following patent publications: U.S. Pat. No. 4,634,771 and EP 281965-A1 and its U.S. equivalent U.S. Pat. No. 4,833,250.

The use of $PCl_5$ as a chlorinating agent used in the preparation of 3-trichloromethylpyridines is known from e.g. U.S. Pat. No. 4,958,025, disclosing the preparation of 3-trichloromethylpyridines starting from nicotinic acid. In U.S. Pat. No. 4,419,514 $PCl_5$, is used in combination with phenylphosphonic dichloride as chlorinating agent for the preparation of PCMP starting from 5-chloro-6-hydroxynicotinic acid.

The production of DCTF can also be accomplished in multi-ton scale production starting from 2-chloro-5-(chloromethyl)pyridine (CCMP) as disclosed in Chinese patent publication number CN 101092392. CCMP can be produced from cyclopentadiene in a 6 step synthesis route, but this process has a very poor atom economy and therefore gives rise to a large waste problem as disclosed in U.S. Pat. No. 5,229,519. Nevertheless, it is this 6 step synthesis route starting from cyclopentadiene that is chosen over alternatives, because of the low cost of cyclopentadiene. The world is therefore in need of a high yielding manufacturing procedure starting from a commercially bulk material and producing DCTF in only few synthetic steps.

It is the object of the present invention to provide a method of producing the intermediate product 2,3-dichloro-5-(trichloromethyl)pyridine (PCMP) in high yields and/or with less by-products, notably less by-products of the type that cannot easily be converted into PCMP. Furthermore, the method omits the intermediate reaction product CCMP. Thus, the present invention present a method to produce 2,3-dichloro-5-trichloromethylpyridine (PCMP) in one single step from easily accessible materials, e.g. nicotinic acid (also known as Vitamin B3). The method of the invention may also be conducted without generating any problematic waste and using minimum unit operation.

The intermediate PCMP can be converted to DCTF by a single subsequent step. In a certain embodiment, the invention provides a two-step method which is easy to operate and economical to produce DCTF from the commercially available bulk material nicotinic acid.

DESCRIPTION OF THE INVENTION

The present invention relates to a method for preparing 2,3-dichloro-5 (trichloromethyl)pyridine of formula [II] by a process which comprises: Reacting a compound of the general formula [I] with $PCl_5$ as chlorinating agent at elevated temperature and pressure;

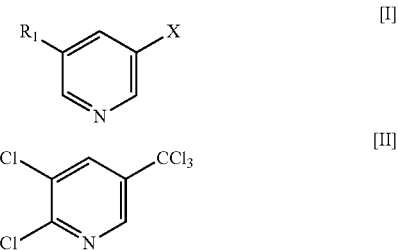

wherein
X is a COOH, $CONH_2$, $CCl_3$, or CN; and
$R_1$ represent H or Cl.

In a preferred embodiment X represents COOH. In a more preferred embodiment the starting material is of formula [I] wherein $R_1$ is H and X is COOH, namely nicotinic acid. The compound of formula [I] wherein $R_1$ is Cl or H and X represents $CCl_3$ is often observed as intermediate products in the course of the reaction starting from any compound of formula [I] with X being as defined above, but different from $CCl_3$ Similar the compound of formula [I] wherein X represents COCl is believed to be formed as an intermediate compound under certain conditions, especially when starting from any of the two compounds wherein X represents COOH.

The reaction may be conducted with or without the presence of a solvent. The solvent can be any aromatic hydrocarbon solvent such as benzene, or any chlorinated solvent such as chlorinated phosphorous compounds such as phosphorous trichloride or phosphoryl chloride, or chlorinated compounds of aliphatic, alicyclic and aromatic hydrocarbons, such as chlorobenzene, monochlorobenzene, dichlorobenzene, chlorotoluene, chloronaphthalene, methylene dichloride, ethylene dichloride, chloroform, carbon tetrachloride, dichloroethane and trichloroethane or mixtures thereof. When a solvent is present it is suitably a chlorinated solvent. In a certain embodiment the chlorinated solvent is also used for the in-situ generation of the chlorinating agent, most preferably the chlorinated solvent is phosphorous trichloride, e.g. which could serve as a source for $PCl_5$ if reacted with a chlorine source such as chlorine gas. Phosphoryl chloride may be formed in the course of the reaction, but if so the amount is relatively small, and is accordingly not considered as a solvent in this context.

The temperature of the process is a compromise between having a high enough temperature to provide a fast reaction, but low enough to have a safe operational pressure and avoiding unwanted side products, decomposition of starting materials, and corrosion of the autoclave. The process can be performed at an elevated temperature, e.g. in one embodiment of the invention, the temperature is preferably in the range of 70 to 200° C., more preferably in the range of 75 to 190° C., and most preferably in the range of 80 to 185° C., but higher temperatures, e.g. as high as 200° C. and above. The higher limit is usually determined by what is practical possible especially on an industrial scale, e.g. depending on reaction equipment and stability of reagents used, and is usually kept below 350° C.

The process is performed at elevated pressure, i.e. at a pressure higher than 1 bar. As such there is no higher limit, but from a practical point of view, the pressure is preferably lower than 50 bar.

The process is performed in one embodiment of the invention at an elevated pressure between 1 to 30 Bar, preferably from 2 to 20 Bar.

In a preferred embodiment of the present invention the pressure of the reaction is higher than 2 bar, preferably higher than 4 bar, more preferably higher than 5 or most preferably higher than 10 bar; and the pressure lower than 50 bar, preferably lower than 40 bar, more preferably lower than 35 bar and most preferably lower than 30 bar. Accordingly, in a preferred embodiment the pressure of the reaction is between 2-50 bar, more preferably 2-40 bar, even more preferably between 2-35 bar and most preferably between 2-30 bar; in a more preferred embodiment the pressure of the reaction is between 4-50 bar, more preferably 4-40 bar, even more preferably between 4-35 bar and most preferably between 4-30 bar; in a more preferred embodiment the pressure of the reaction is between 5-50 bar, more preferably 5-40 bar, even more preferably between 5-35 bar and most preferably between 5-30 bar; and in an even more preferred embodiment the pressure of the reaction is between 10-50 bar, more preferably 10-40 bar, even more preferably between 10-35 bar and most preferably between 10-30 bar. Under these preferred pressure conditions the reaction is preferably conducted at elevated temperatures higher than 160° C., more preferably higher than 180° C., even more preferably higher than 185° C., most preferably higher than 190° C. and utmost preferably higher than 200° C. The higher limit is usually determined by what is practical possible especially on an industrial scale, but is usually kept below 350° C., preferably lower than 300° C. and most preferably lower than 250° C. Accordingly, in a preferred embodiment the temperature is kept between 160-350° C., preferably between 180-350° C. more preferably between 185-350° C., most preferably between 190-350° C. and utmost preferably between 200-350° C.; in a more preferred embodiment the temperature is kept between 160-300° C., preferably between 180-300° C. more preferably between 185-300° C., most preferably between 190-300° C. and utmost preferably between 200-300° C.; and an even more preferred embodiment the temperature is kept between 160-250° C., preferably between 180-250° C., more preferably between 185-250° C., most preferably between 190-250° C. and utmost preferably between 200-250° C.

The amount of chlorinating agent relative to the compound [I], i.e. $PCl_5$, used in the process may vary dependent on the specific process conditions, but preferably the amount of chlorinating agent is between 2 to 15 moles, more preferably between 2 to 10 moles per mole of the compound of the general formula [I]. In a preferred embodiment the amount of chlorinating agent is between 3 to 10 moles, more preferably between 3 to 8 moles, even more preferably between 3 to 6 moles and most preferably between 3 to 5 moles per mole of the compound of the general formula [I].

The $PCl_5$ may be added directly to the reaction vessel either at once or continuously, but may also be prepared, in total or in part of the total amount of chlorinating agent, prior to or during the course of the reaction e.g. from an appropriate amount of $PCl_3$ reacted with a chlorine source, e.g. the reaction between $PCl_3$ and $Cl_2$ being reacted for example in equimolar amounts. $PCl_3$ is formed during the reaction, and accordingly can be used for the generation of $PCl_5$ either during or after completion of the reaction, e.g. for reuse in subsequent reactions according to the invention. Accordingly, the amount of $PCl_5$ used needs not necessarily initially to be present, but may be (re-)generated during the reaction. The $PCl_5$ may be added along with $Cl_2$. It has been found that if any or all the $PCl_5$ is generated from the reaction between $PCl_3$ and $Cl_2$, and if $Cl_2$ has been used in excess of $PCl_3$, the reaction provides a high yield of the desired compound [II], but also several undesired over-chlorinated compounds (such as 2,3,4-trichloro-5-(trichloromethyl)pyridine and 2,3,4,6-tetrachloro-5-(trichloromethyl)pyridine), that are not easily separated from the desired end-product and generates unwanted waste streams. On the other hand, if $Cl_2$ has been used in equimolar amounts or less in respect of the $PCl_3$, the compound [II] is formed in good yield along with the compound 2-chloro-5-(trichloromethyl)pyridine, but with only small amounts of the undesired over-chlorinated compounds. The ratio varies in accordance with the reaction conditions chosen, but usually in an approximately 2:1 ratio between the 2,3-dicloro- and 2-chloro-5-(trichloromethyl)pyridine. The 2-chloro-5-(trichloromethyl)pyridine however, is easily converted to the compound [II] using known reaction conditions, e.g. using chlorine gas with or without the presence of one or more catalysts, e.g. as described in patent applications nos. U.S. Pat. Nos. 4,636,565, 4,331,811, 4,309,548 and EP246349-A1. This conversion can be performed without having to separate the compound [II] from the previous reaction according to the invention, i.e. using a one-pot process overall. It is however advantageous to remove any left amounts of $PCl_3$ prior to the addition of the chlorine gas. Thus, the reaction conditions in terms of amount of chlorine gas used, is a tradeoff between obtaining a high yield directly of the compound [II] or high selectivity that requires additional treatment as to provide an even higher yield of the compound [II]. The reactions conditions are preferably so selected as to provide an overall yield of the compound [II] in more than 60% (based on amount of starting compound [I]), preferably more than 70%, more preferably 80% or higher and most preferably 90% or higher.

Accordingly, in an embodiment of the present invention, any amount of the intermediate compound 2-chloro-5-(trichloromethyl)pyridine formed in the course of the reaction is converted through a secondary chlorination to the compound of formula [II] by subjected the 2-chloro-5-(trichloromethyl)pyridine to a chlorination step, i.e. using a chlorinating agent, e.g. $Cl_2$, optionally in the presence of a catalyst. This secondary chlorination follows after the first reaction as described herein is judged to be complete or caused to stop, e.g. no further conversion of the starting compound [I] is taking place. The optional catalyst can be selected among metal based catalyst including chlorides, bromides, oxychlorides, oxybromides, phosphines and acetates, particularly metal chlorides and bromides (including oxychlorides and oxybromides) such as $FeCl_3$, $AlCl_3$, $RuCl_3$, $SnCl_4$, $WCl_6$, $MoCl_5$, $MoCl_4O$, or $WCl_4O$ and metal carbonyls such as $Mo(CO)_6$ or $W(CO)_6$; or phosphines, such as $(Ph)_3P$, $(Ph)_3P=O$; boranes such as $BCl_3$; as well as any mixtures thereof. The amount of catalyst(s) is preferably between 0.01 to 20 mol % relative to the 2-chloro-5-(trichloromethyl)pyridine, more preferably 0.05 to 10 mol % and most preferably 0.5 to 5 mol %. In a preferred embodiment the chlorination of the 2-chloro-5-(trichloromethyl) pyridine to the compound of formula [II] is carried out without isolating the 2-chloro-5-(trichloromethyl)pyridine from the previous reaction and preferably with removal of any remaining $PCl_3$ prior to the addition of the chlorinating agent. The chlorinating agent is preferably used in excess of the 2-chloro-5-(trichloromethyl)pyridine. The chlorination needs not necessarily be carried out at elevated temperature and optionally at elevated pressure. However, elevated pressure and temperature does influence the speed of the reaction. Accordingly the reaction is preferably carried out at a temperature above 70° C. and preferably in the range between 100 to 250° C., while the pressure is in the range between 1 to 30 Bar, preferably from 2 to 20 Bar.

The HCl gas formed during the reaction according to the invention is maintained in the reaction vessel to the extend the desired reaction pressure is maintained throughout the reaction, or within a preferred interval. The reaction vessel is advantageously so selected as to withstand the reaction conditions herein described and preferred, especially the temperature and pressure conditions but preferably of a material that is inert to the starting materials and other reagents used as well as the end-product formed and any bi-products.

In one embodiment of the invention the compound of formula [I] is used in the form of its salt, e.g. produced by reacting the compound of formula [I] with an acid having pKa value less than 3.5. Preferably, the acid is a mineral acid such as hydrochloric acid producing the hydrochloric salt.

In another embodiment of the invention, the compound of formula [II] may be converted to the compound of formula [III] by subjecting the compound of formula [II] to a fluorination step:

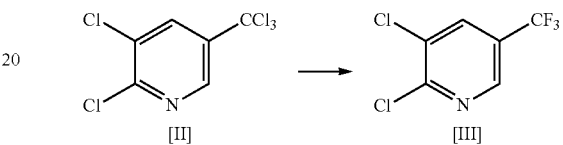

The fluorinating agent used in such process may be selected among hydrogen fluoride (HF), Potassium fluoride (KF), antimony trifluoride ($SbF_3$), or antimony pentafluoride ($SbF_5$). The fluorinating agent is preferably used in excess of the compound [II]. The fluorination reaction is preferably carried out at a temperature above 100° C. and preferably in the range between 100 to 250° C., while the pressure is preferably higher than 5 bar and preferably in the range between 5 to 40 Bar, more preferably from 10 to 30 Bar.

The compound of formula [III] may further be converted to a pesticidal active compound, e.g. a herbicidal, insecticidal or fungicidal active compound such as fluazinam, fluopicolide, haloxyfop, chlorfluazuron and fluazuron. An examples of the preparation of fluazinam and fluopicolide is as illustrated below:

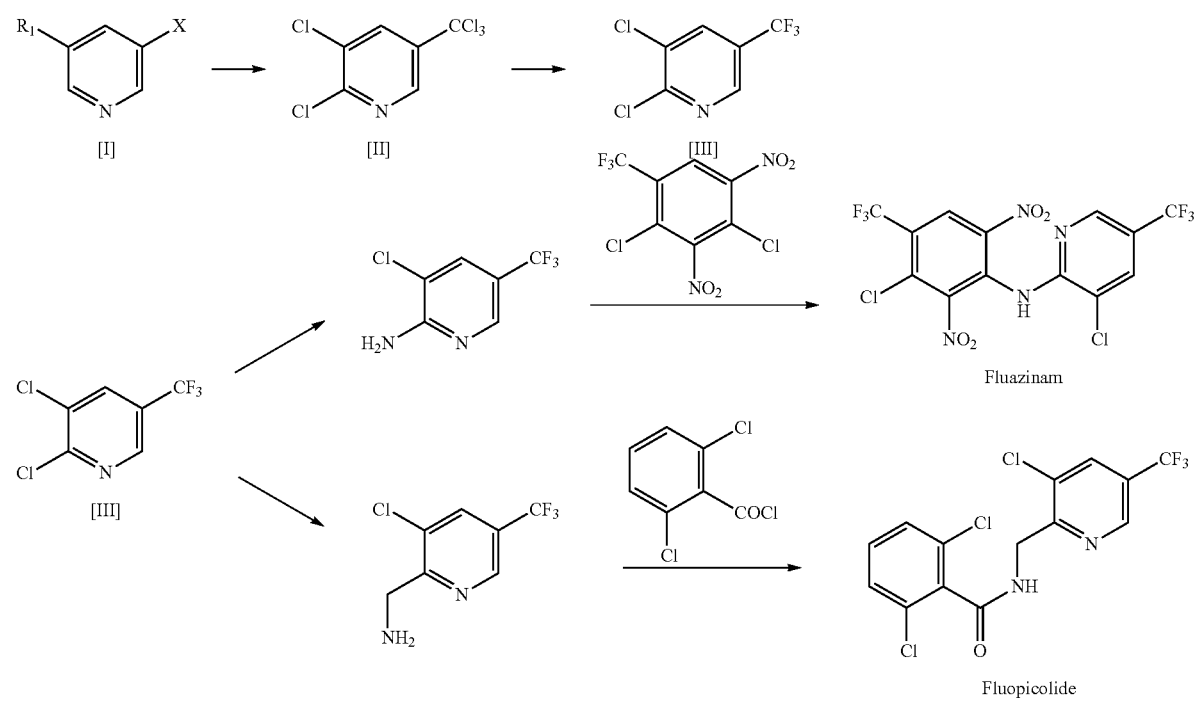

The process of the invention is carried out in an autoclave by reacting a compound of general formula [I] with $PCl_5$ as the chlorinating agent. The reaction mixture is heated to elevated temperature and pressure for a certain period of time. After the reaction is judged to be complete, a base may be added to the resulting suspension. Hereafter, the reaction mixture is worked up and the product isolated using conventional techniques well known to a skilled chemist.

In an alternative process, the invention is carried out in an autoclave by reacting a compound of general formula [I] with $PCl_5$ as the chlorinating agent in the presence of a solvent. The reaction mixture is heated to elevated temperature and pressure for a certain period of time. After the reaction is judged to be complete, a base may be added to the resulting suspension. Hereafter, the reaction mixture is worked up and the product isolated using conventional techniques well known to a skilled chemist.

In a large laboratory scale, the invention is carried out in an autoclave by reacting a compound of general formula [I] with $PCl_5$ as the chlorinating agent. The reaction mixture is heated to elevated temperature and pressure for a certain period of time. After the reaction is judged to be complete, the resulting suspension was heated to reflux to recover the phosphorous trichloride and phosphoryl chloride. The product can be obtained by distillation.

In any of the above methods for carrying out the reaction according to the invention, the $PCl_5$ may be added directly to the reaction vessel either at once or continuously, but may also be prepared, in total or in part of the total amount of chlorinating agent, prior to or during the course of the reaction e.g. from an appropriate amount of $PCl_3$ reacted with a chlorine source, e.g. the reaction between $PCl_3$ and $Cl_2$. In a preferred embodiment the $PCl_5$ is generated in-situ.

The starting compounds of general formula [I] are known and either available on a commercial scale or are easily prepared according to known methods. The compounds of the formula [I] wherein X represents COCl may be prepared from the corresponding acid compounds (X represents COOH) using standard methods, e.g. using various chlorinating agents such as $SOCl_2$, $COCl_2$, $(COCl)_2$, $PCl_5$ or $POCl_3$. The acid chloride is formed as an intermediate compound if the initial starting material is the acid, i.e. it is formed in-situ in the reaction vessel. Accordingly, if the starting material is a compound [I] where X represents COOH, up to one equivalent of the total amount of $PCl_5$ may be substituted with any chlorinating agent feasible for preparing acid chlorides, e.g. those mentioned previously. Thus, in accordance with the preferred amount of the chlorinating agent, $PCl_5$, which is used in amounts between 2 to 25 moles per mole of the compound of the general formula [I], up to one mole of $PCl_5$ per mole of the compound of the general formula [I] may be substituted e.g. with the above mentioned chlorinating agents.

EXAMPLES

Example 1

Conversion of Nicotinic acid to
2,3-dichloro-5-(trichloromethyl)pyridine

Nicotinic acid (2 g, 16.25 mmole) and phosphorous pentachloride (27 g, 130 mmole) was mixed in a 50 ml Teflon autoclave. The autoclave was closed and heated in a 180° C. warm metal block. After 48 hours was the autoclave cooled to 25° C. and opened. The resulting suspension was quenched in a mixture of NaOH (10%) and dichloromethane under stirring, keeping the temperature below 30° C. The phases were separated and the organic phase was evaporated to dryness to get the crude product. The product was hereafter distilled and 2,8 g of 2,3-dichloro-5-(trichloromethyl)pyridine was obtained (65% yield).

Example 2

Large Laboratory Scale Conversion of Nicotinic acid to 2,3-dichloro-5-(trichloromethyl)pyridine Nicotinic acid (14 g, 0.114 mole) and phosphorous trichloride (126 g, 0.91 mole) were added to an autoclave. Stirring was adjusted to 300 rpm and temperature adjusted to 80° C. At 80° C. chlorine gas was added to head space (16 g, 0.228 mole). The temperature is allowed to go up to 120° C. At 120° C. another portion of chlorine gas is added (48.5 g, 0.68 mole) followed by heating to 165° C. for 114 hours, which resulted in a pressure of 15 Bar. The autoclave was cooled to 25° C. and ventilated to a Caustic Lye scrubber. The resulting solution was heated to reflux to recover phosphorous trichloride and phosphoryl chloride by distillation. The product was hereafter distilled and 21.7 g of 2,3-dichloro-5-(trichloromethyl)pyridine was obtained giving 72% yield not correlated for purity.

Example 3

Conversion of
2,3-dichloro-5-(trichloromethyl)pyridine to
2,3-dichloro-5-(trifluoromethyl)pyridine 2,3-dichloro-5-(trichloromethyl)pyridine (5 g, 18.84 mmole), iron(III) chloride (0.153 g, 0.942 mmole) and hydrogen fluoride (2.423 g, 85 mmole) in pyridine solution (70%) was added to an autoclave and heated to 175° C. over night. The autoclave was cooled to 130° C. and left for stirring additional 5 hours, followed by cooling to 25° C. and opened carefully leaving gas phase through a Caustic Lye scrubber. The crude was dissolved in dichloromethane, washed with 1 M NaOH (aq) and water. The organic phase was removed by distillation and the product was obtained by distillation (3.0 g, 73% yield).

Example 4

Conversion of Nicotinic acid to
2,3-dichloro-5-(trichloromethyl)pyridine

Using a similar setup as described in example 1, a series of experiments were carried out using various amounts of chlorinating agent and at a temperature of 175° C., pressure set between 20 and 50 bar and with results in accordance with the below table 1.

TABLE 1

| | 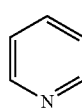 | 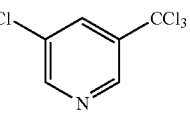 | 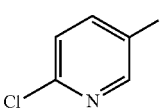 | 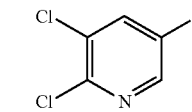 | Others |
|---|---|---|---|---|---|
| 2.5 eq. PCl₅ + 4.5 eq. Cl₂ | 0% | 3% | 2% | 74% | 21% |
| 2.5 eq. PCl₅ + 6 eq. Cl₂ | 0% | 0% | 1% | 66% | 33% |
| 4 eq. PCl₅ + 4 eq. Cl₂ | 0% | 4% | 8% | 79% | 9% |

(Others include over-chlorinated pyridines, pyridines chlorinated in other positions and under-chlorinated analogs of the above compounds, e.g. $CHCl_2$ and $CH_2Cl$ substituted pyridines).

Example 5

Conversion of Nicotinic acid to 2,3-dichloro-5-(trichloromethyl)pyridine

Using a similar setup as described in example 1, a series of experiments were carried out with 4 molar eq. of PCl₅ at various temperatures and a pressure reaching between 25 and 40 bar after completion. Results are provided in table 2.

TABLE 2

| Experiment | 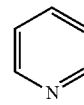 | 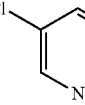 | 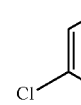 | 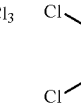 | Others |
|---|---|---|---|---|---|
| 175° C. (96 h) | 18% | 5% | 19% | 50% | 8% |
| 185° C. (72 h) | 19% | 3% | 22% | 51% | 2% |
| 195° C. (72 h) | 4% | 1% | 32% | 60% | 3% |
| 210° C. (16 h) | 1% | 0% | 32% | 62% | 5% |
| 220° C. (16 h) | 0% | 0% | 35% | 61% | 4% |
| 225° C. (16 h) | 0% | 0% | 33% | 63% | 4% |

Example 6

Conversion of Nicotinic acid to 2,3-dichloro-5-(trichloromethyl)pyridine

Using a similar setup as described in example 1, a series of experiments were carried out using various amounts of PCl₅, at a temperature set at 210° C., and at pressure reaching between 25 and 40 bar after completion. Results in accordance with the below table 3.

Example 7

Conversion of Nicotinic acid to a Mixture of 2-chloro-5-(trichloromethyl)pyridine and 2,3-dichloro-5-(trichloromethyl)pyridine To a 250 ml Berghof autoclave with PTFE lining was added Nicotinic acid (20 g, 162 mmole) and phosphorous pentachloride (139 g, 668 mmole). The autoclave was closed and heated to 210° C. for 14 hours. During the heating an exotherm was observed around a temperature of 130° C. bringing the temperature to 190° C. and a pressure increase from 2 bar to 8 bar within 2 minutes. The heating was continued to 210° C. After the 14 hours the pressure had increased to 37 Bar. The autoclave was cooled to room temperature, ventilated to a scrubber, opened and quantified by GC indicating a yield of 2-chloro-5-(trichloromethyl)pyridine of 33% compared to the Nicotinic acid starting material and a yield of 2,3-dichloro-5-(trichloromethyl)pyridine 60%.

TABLE 3

| | 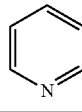 | 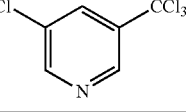 | 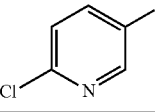 | 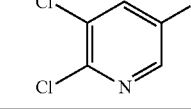 | Others |
|---|---|---|---|---|---|
| 3.75 eq PCl₅ | 5% | 1% | 35% | 53% | 7% |
| 4.5 eq PCl₅ | 0% | 2% | 29% | 63% | 6% |
| 6 eq PCl₅ (185° C., 64 h) | 0% | 3% | 24% | 66% | 9% |
| 8 eq PCl₅ (185° C., 64 h) | 3% | 7% | 17% | 69% | 4% |

Example 8

Preparation of 2,3-dichloro-5-(trichloromethyl)pyridine from the mixed reaction media of Example 7

A series of experiments were carried out using the setup from example 7, and the individual resulting reaction mixtures, without any isolation of the 2,3-dichloro-5-(trichloromethyl)pyridine, were placed in a round bottomed flask and any remaining $PCl_3$ removed by distillation at normal pressure. In each experiment the resulting solution was returned to the autoclave, cooled with a dry-ice/acetone bath and 3-6 eq $Cl_2$ per eq. 2-chloro-5-(trichloromehyl)pyridine added and optionally a catalyst was also present. The autoclave was heated to 140-175° C. for 3-16 hours. Results in accordance with the below table 4.

TABLE 4

| Reaction condition | 3-CCl₃-pyridine | 3-Cl-5-CCl₃-pyridine | 2-Cl-5-CCl₃-pyridine | 2,3-diCl-5-CCl₃-pyridine | Others |
|---|---|---|---|---|---|
| 140° C., FeCl₃ | 1% | 1% | 13% | 78% | 7% |
| 140° C., FeCl₃ Excess Cl₂ | 0% | 0% | 10% | 83% | 7% |
| 140° C., FeCl₃ Excess Cl₂ | 0% | 0% | 3% | 89% | 8% |
| 140° C., no cat. High excess Cl₂ | 0% | 0% | 6% | 86% | 8% |
| 175° C., FeCl₃ Excess Cl₂ | 0% | 4% | 8% | 79% | 9% |
| 170° C., WCl₆ Excess Cl₂ | 0% | 0% | 0% | 92% | 8% |

Example 9

Preparation of 2,3-dichloro-5-(trichloromethyl)pyridine from various compounds of the formula [I].

The starting material of formula [I] (50 mmole) and $PCl_5$ (1 or 2 eq.) was mixed in a 50 ml teflon autoclave. The autoclave was closed and heated in a 210° C. warm metal block. After 16 hours the autoclave was cooled to 25° C. and opened. The resulting solution was analyzed by GC with results according to table 5.

TABLE 5

| Starting material | 3-CCl₃-pyridine | 3-Cl-5-CCl₃-pyridine | 2-Cl-5-CCl₃-pyridine | 2,3-diCl-5-CCl₃-pyridine | Others |
|---|---|---|---|---|---|
| 3-(trichloromethyl)pyridine | 2% | 7% | 39% | 46% | 6% |
| 3-chloro-5-(trichloromethyl)pyridine | 0% | 6% | 0% | 87% | 7% |
| Comparative | | | | | |
| 2-chloro-5-(trichloromethyl)pyridine | 0% | 0% | 99% | 0.5% | 0.5% |

In comparison, starting with the compound 2-chloro-5-(trichloromethyl)pyridine only very low conversion to the compound [II] is observed.

Example 10

Conversion of Nicotinic acid to 2,3-dichloro-5-(trichloromethyl)pyridine

Nicotinic acid (50 g, 0.4 mole) and phosphorous trichloride (223 g, 1.6 mole) were added to an 0.5 L jacketed autoclave, connected to a cooling-heating circulator. The temperature of the reaction mixture was adjusted to 120° C. and chlorine gas (115 g, 1.6 mole) was added to head space from a pressure bottle. During addition of chlorine was the temperature maintained between 120° C. and 140° C. with cooling circulation on the jacket. After addition of chlorine gas is the pressure in the autoclave around 3 bar. The temperature is increased to 180° C. (will be preferred to increase to 210° C., but this was not possible in the current setup) and kept there for 144 hours (210° C. will finish reaction in 16 hours). During the reaction HCl(g) was removed through a scrubber periodically to keep pressure between 12 and 16 bar. The autoclave was then cooled to 25° C. and ventilated to a Caustic Lye scrubber. The resulting solution was heated to reflux to recover phosphorous trichloride by distillation. The autoclave was closed again and chlorine gas (50 g, 0.5 mole) was added at room temperature. The resulting mixture was heated to 130° C. and pressure was kept below 15 bar by removing HCl(g) above a condenser to a caustic lye scrubber. When pressure becomes stable (typically after 2-4 hours), the reaction is considered completed and the autoclave cooled down. If analysis shows otherwise, the final chlorination procedure can be repeated. The reaction mixture was then transferred to a round bottomed flask and phosphoryl chloride was removed by distillation. In case there is any solid PCl5 in the reactor, it can be converted to phosphoryl chloride with a few drops of water and transferred together with the main reaction mixture. Upon distillation of phosphoryl chloride—the crude product was obtained by addition to ice cold water, stirred for 10 minutes and allowed to stand for separation for 1 hours at 25° C. The lower organic phase is separated from the acidic water phase and the product hereafter distilled to give 80 g of 2,3-dichloro-5-(trichloromethyl)pyridine with a purity of 96% (75% yield).

Example 11

Conversion of 2,3-dichloro-5-(trifluoromethyl)pyridine to Fluazinam 2,3-dichloro-5-(trifluoromethyl)pyridine (26,75 g, 0.125 mole) and water (25 ml) was added to an autoclave. The autoclave was closed and liquid ammonia (45 g, 2,85 mole) was added from a pressure bottle. The autoclave was heated to 80° C. for 9 hours at a pressure between 22 and 18 bar. The reaction was cooled to room temperature and the intermediate, 2-amino-3-chloro-5-(trifluoromethyl)pyridine was obtained by filtration, washing with water and drying (22 g, 90%). The intermediate was dissolved in acetonitril (230 ml). The solution was cooled to 5° C. and KOH (s., 12 g, 0.22 mole) was added. A solution of 2,4-dichloro-3,5-dinitro-5-(trifluoromethyl)benzene (25 g, 0.08 mole) in acetonitrile (230 ml) was added over 15 minutes with continuous cooling. The temperature was raised to 25° C. for four hours followed by a a temperature increase and kept at 40° C. for two hours. The mixture was added to 1500 ml of water, neutralized to a pH around 4 with 4N HCl (aq) and extracted with isopropyl acetate (2×750 ml). The organic phase was evaporated to dryness to get crude Fluazinam (43 g, 70% yield, 60% purity). The Fluazinam can be further purified by recrystallization.

Example 12 (Comparative)

Conversion of Nicotinic acid using an Open Reactor

Thionyl chloride (250 ml, 3.4 mole) was mixed with Nicotinic acid (123 g, 1 mole) in a round bottomed flask with a mechanical stirrer. The suspension was heated to 55° C. for 15 minutes followed by distillation of excess thionyl chloride. To the resulting reaction mixture was added phosphorous trichloride (275 g, 2 mole) followed by chlorine gas (140 g, 2 mole). The mixture was heated slowly—in an oil bath—to 150° C. Heating took approximately 5 hours and phosphoryl chloride was distilled off simultaneously. After 1 hour at 150° C. was the reaction mixture analysed with GC. Results are shown in below table 6.

As seen from the table the yield of the compound [II] is low if the reaction is not conducted at elevated pressure.

What is claimed is:

1. A method for preparing 2,3-dichloro-5-(trichloromethyl)pyridine of formula [II] by a process which comprises the steps:
   (1) preparing a reaction mixture comprising a compound of the general formula [I] and PCl5,

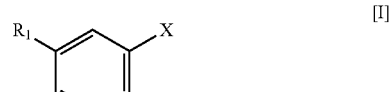

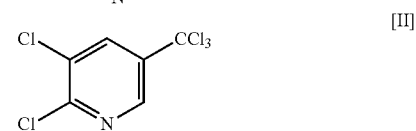

wherein
(i) X is COOH, CONH2, CCl3, or CN;
(ii) R1 represents H or Cl;
and
(iii) PCl5 acts as a chlorinating agent; and
(2) reacting said mixture at a pressure above 1 bar and a temperature above about 70° C. and below about 350° C.

2. The method according to claim 1, wherein the reaction mixture further comprises at least one additional chlorinating agent selected from the group consisting of Cl2, PCl3, SOCl2, COCl2, (COCl)2, POCl3, or mixtures thereof.

3. The method according to claim 2, wherein the additional chlorinating agent is Cl2.

4. The method according to claim 1 wherein X of the compound of formula [I] represents COOH.

5. The method according to claim 1, wherein the temperature of the reaction is above 70° C.

6. The method according to claim 1, wherein the temperature of the reaction is in the range between 70° C. to 200° C.

7. The method according to claim 1, wherein the temperature of the reaction is above 160° C.

8. The method according to claim 1, wherein the temperature of the reaction is below 350° C.

9. The method according to claim 1, wherein the pressure of the reaction is above 2 bar.

10. The method according to claim 1, wherein the pressure of the reaction is below 50 bar.

11. The method according to claim 1, wherein the pressure of the reaction is in the range of 2 to 30 bar.

12. The method according to claim 1, wherein the pressure of the reaction is above 30 bar.

TABLE 6

| | | | | | |
|---|---|---|---|---|---|
| (nicotinoyl chloride) | (3-CCl3-pyridine) | (3-Cl-5-CCl3-pyridine) | (2-Cl-5-CCl3-pyridine) | (2,3-diCl-5-CCl3-pyridine) | Others |
| 5% | 92% | 2% | 0.2% | 0.1% | 0.7% |

13. The method according to claim 1, wherein the temperature of the reaction is in the range of 160° C. to 250° C., and the pressure of the reaction is in the range of 10 bar to 30 bar.

14. The method according to claim 1, wherein the reaction is conducted in the absence of solvent.

15. The method according to claim 1, wherein the reaction is conducted in the presence of a solvent.

16. The method according to claim 15, wherein the solvent is a chlorinated solvent.

17. The method according to claim 15, wherein the solvent is phosphorous trichloride, phosphoryl chloride, monochlorobenzene, dichlorobenzene, chlorotoluene, chloronaphthalene, methylene dichloride, ethylene dichloride, chloroform, carbon tetrachloride, dichloroethane, trichloroethane, or mixtures thereof.

18. The method according to claim 1, wherein the $PCl_5$ is generated in-situ, in part or in total.

19. The method according to claim 18, wherein the $PCl_5$ is generated from a reaction between $PCl_3$ and $Cl_2$.

20. The method according to claim 19, wherein $Cl_2$ is used in equimolar amounts or less in respect of the $PCl_3$.

21. The method according to claim 1, wherein the total amount of chlorinating agent is between 2 to 15 moles per mole of the compound of the general formula [I].

22. The method according to claim 1, further comprising a second chlorination step.

23. The method according to claim 22, wherein $Cl_2$ is added in the second chlorination step to produce the compound of formula [II].

24. The method according to claim 22, wherein $PCl_3$, if present, is removed from the reaction mixture prior to the secondary chlorination.

25. The method according to claim 22, wherein a catalyst is provided to promote the secondary chlorination.

26. The method according to claim 25, wherein the catalyst is selected from the group consisting of: metal chlorides, oxychlorides, carbonyls, phosphines, boranes or mixtures thereof.

27. The method according to claim 1, further comprising a fluorination step to fluorinate the compound of formula [II] to obtain the compound of formula [III]

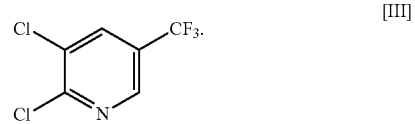 [SMILES: FC(F)(F)c1cnc(Cl)c(Cl)c1]

28. The method according to claim 27, wherein the compound of formula [III] is further converted to a pesticidal active compound.

29. The method according to claim 28, wherein the pesticidal active compound is a herbicide, an insecticide or a fungicide.

30. The method according to claim 29, wherein the pesticidal active compound is fluazinam, fluopicolide, haloxyfop, chlorfluazuron or fluazuron.

31. The method according to claim 26, wherein the metal chloride catalyst is selected from the group consisting of: $FeCl_3$; $AlCl_3$; $RuCl_3$; $SnCl_4$; $WCl_6$; $MoCl_5$; $MoCl_4O$; $WCl_4O$ and mixtures thereof.

32. The method according to claim 26, wherein the carbonyl catalyst is selected from the group consisting of: $Mo(CO)_6$; $W(CO)_6$; and mixtures thereof.

33. The method according to claim 26, wherein the phosphine catalyst is selected from the group consisting of: $(Ph)_3P$ or $(Ph)_3P=O$; and mixtures thereof.

34. The method according to claim 26, wherein the borane catalyst is $BCl_3$.

* * * * *